United States Patent [19] [11] 4,361,579
Munakata et al. [45] Nov. 30, 1982

[54] ORGANOGERMANIUM COMPOUNDS

[75] Inventors: Tomohiko Munakata, Nakatsu; Chiaki Tashiro, Yoshitomi; Yutaka Maruyama, Nakatsu, all of Japan

[73] Assignee: Yoshitomi Pharmaceutical Industries, Ltd., Osaka, Japan

[21] Appl. No.: 188,787

[22] Filed: Sep. 19, 1980

[30] Foreign Application Priority Data

Sep. 19, 1979 [JP] Japan ............................ 54-121027
Jan. 11, 1980 [JP] Japan ............................ 55-2461

[51] Int. Cl.³ .................... C07F 7/30; A01N 9/00; A61K 31/28; A61L 13/00
[52] U.S. Cl. .................... 424/287; 260/429.7; 544/64; 546/2
[58] Field of Search ............... 260/429 R; 424/287; 544/64; 546/2

[56] References Cited

U.S. PATENT DOCUMENTS

| | | | |
|---|---|---|---|
| 3,651,018 | 3/1972 | Schade et al. | 260/429 R X |
| 3,689,516 | 9/1972 | Asai et al. | 260/429 R |
| 3,812,167 | 5/1974 | Pahk | 260/429 R |
| 4,066,678 | 1/1978 | Sato et al. | 260/429 R |
| 4,271,084 | 6/1981 | Ishikawa et al. | 260/429 R |

Primary Examiner—Helen M. S. Sneed
Attorney, Agent, or Firm—Sughrue, Mion, Zinn, Macpeak & Seas

[57] ABSTRACT

A polycondensation product of a germanium trihydroxide compound of the formula:

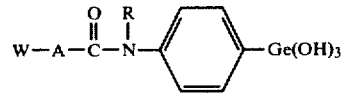

wherein W is hydrogen, alkyl, halogen, alkoxycarbonyl, carboxy, aryl, cycloalkyl which may be substituted, cycloalkenyl, heteroaryl or a group of the formula: $(R^1)(R^2)N-$ wherein $R^1$ and $R^2$ are each lower alkyl or $R^1$ and $R^2$ together with the adjacent nitrogen atom form a group of the formula:

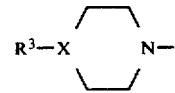

wherein $R^3$ is hydrogen, lower alkyl, phenyl which may be substituted, aralkyl, acyl, acylamino or heteroaryl, and X is $-N=$, $-CH=$ or

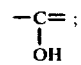

A is a bond, alkylene, alkenylene, $-CO-Y-$, $-CONH-Y-$, $-O-Y-$, $-S-Y-$ or

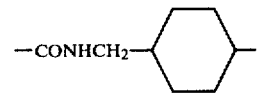

(Y is alkylene); and R is alkyl. Such compounds are useful as agents for treating immune diseases.

12 Claims, No Drawings

ORGANOGERMANIUM COMPOUNDS

This invention relates to organogermanium compounds which are therapeutically useful as agents for treating immune diseases.

According to the present invention, there is provided a polycondensation product of a germanium trihydroxide compound of the formula:

$$W-A-\overset{O}{\underset{\|}{C}}-\underset{R}{\underset{|}{N}}-\langle\text{phenyl}\rangle-Ge(OH)_3 \quad (I)$$

wherein W is hydrogen, alkyl (methyl, ethyl, propyl, isopropyl, butyl, sec-butyl, tert-butyl, pentyl, etc.), halogen (Cl, Br, etc.), alkoxycarbonyl (methoxycarbonyl, ethoxycarbonyl, etc.), carboxy, aryl (phenyl, naphthyl, dihydronaphthyl, indanyl, indenyl, etc.), and phenyl may be substituted by at least one substituent at any position(s), each substituent being independently, for example, halogen (F, Cl, Br, I), lower alkyl (methyl, ethyl, propyl, etc.), lower alkoxy (methoxy, ethoxy, propoxy, etc.), (nitro, cyano, carboxy, alkoxycarbonyl or acetylamino), cycloalkyl which may be substituted (cyclopropyl, 2,2-dimethyl-3-(2-methyl-1-propenyl)cyclopropyl, cyclohexyl, etc.), cycloalkenyl (cyclohexenyl etc.), heteroaryl (furyl, thienyl, pyridyl, etc.) or a group of the formula: $(R^1)(R^2)N-$ wherein $R^1$ and $R^2$ are each lower alkyl or $R^1$ and $R^2$ together with the adjacent nitrogen atom form a group of the formula:

$$R^3-X\underset{\smile}{\overset{\frown}{\bigcirc}}N-$$

wherein $R^3$ is hydrogen, lower alkyl, phenyl which may be substituted by, for example, halogen, lower alkoxy or trifluoromethyl, aralkyl (benzyl, phenethyl, 3-phenylpropyl, etc.), acyl (acetyl, propionyl, benzoyl, 4-aminobenzoyl, etc.), acylamino or heteroaryl (2,3-dihydro-2-oxobenzimidazolyl etc.), and X is $-N=$, $-CH=$ or $$-\underset{\underset{OH}{|}}{C}=\ ;$$

A is a bond, alkylene (methylene, ethylene, propylene, isopropylidene, trimethylene, 2-methyltrimethylene, etc.), alkenylene (vinylene, propenylene, 2-methylpropenylene, etc.), $-CO-Y-$, $-CONH-Y-$, $-O-Y-$, $-S-Y-$ or $$-CONHCH_2-\langle\text{cyclohexyl}\rangle-$$

(Y is alkylene); and R is alkyl such as mentioned for W.

The organogermanium compounds of the present invention can be produced by one of the following methods:

Method I

This method, to be applied for the production of compounds wherein W is other than carboxy or a group of the formula: $(R^1)(R^2)N-$, comprises reacting a compound of the formula:

$$(RNH-\langle\text{phenyl}\rangle-GeO)_2O \quad (II)$$

wherein R is as defined above, with a functional derivative of a carboxylic acid of the formula:

$$W-A-COOH \quad (III)$$

wherein W and A are as defined above. The functional derivative of a carboxylic acid of formula (III) is, for example, an acid halide (acid chloride, acid bromide, etc.), an acid anhydride or a mixed acid anhydride with an alkyl chlorocarbonate (ethyl chlorocarbonate, isopropyl chlorocarbonate, etc.), preferably an acid halide.

The reaction is usually carried out in an inert solvent such as benzene, toluene, xylene, chloroform, dichloroethane, ethyl acetate, dioxane, tetrahydrofuran, ethyleneglycol dimethyl ether, ethyleneglycol diethyl ether, dimethylformamide, dimethyl sulfoxide, pyridine, water or a mixture thereof, at room temperature to the boiling point of the solvent employed, for several minutes to ten-odd hours. Each mole of a starting compound of formula (III) is reacted with one to ten moles, preferably 1.3 to 4 moles, of a starting compound of formula (II).

The product thus obtained wherein W is alkoxycarbonyl can be hydrolyzed in a conventional manner to a compound wherein W is carboxy.

Method II

This method, to be applied for the production of compounds wherein W is a group of the formula $(R^1)(R^2)N-$, comprises reacting a polycondensation product of a compound of the formula:

$$CH_2=\underset{\underset{R^4}{|}}{C}-\overset{O}{\underset{\|}{C}}-\underset{\underset{R}{|}}{N}-\langle\text{phenyl}\rangle-Ge(OH)_3 \text{ or} \quad (I\text{-a})$$

$$Z-A-\overset{O}{\underset{\|}{C}}-\underset{\underset{R}{|}}{N}-\langle\text{phenyl}\rangle-Ge(OH)_3 \quad (I\text{-b})$$

wherein R and A are as defined above, $R^4$ is hydrogen or methyl, and Z is a reactive ester residue, especially Cl or Br, with a compound of the formula:

$$\underset{R^2}{\overset{R^1}{\diagdown}}NH \quad (IV)$$

wherein $R^1$ and $R^2$ are as defined above.

The reaction is usually carried out in an inert solvent such as methanol, ethanol, isopropanol, benzene, toluene, chloroform, dioxane, tetrahydrofuran, acetone, methyl ethyl ketone, water or a mixture thereof, if necessary in the presence of a deacidifying agent such as sodium carbonate, potassium carbonate or precipitated calcium carbonate, at room temperature to the boiling point of the solvent employed, for several ten minutes to ten-odd hours.

The starting compounds of formula (II) can be prepared by reacting an aniline derivative with germanium tetrachloride under heating as described by H. Bauer and K. Burshkies in "Chemishe Berichte" vol. 65, pp. 956–960 (1932). In this article, the products so formed are described to be the germanic anhydride (i.e., dimer) but it seems that a polymeric form is correct from consideration of the physical properties.

After completion of the reaction, the reaction mixture is washed with water, an aqueous alkali bicarbonate solution, an aqueous alkali carbonate solution or an aqueous alkali hydroxide solution. If necessary, acid-washing and alkali-washing are repeated to remove the unreacted and excess starting materials. The products are further purified, for example, by treatment with activated charcoal, by column chromatography or by salt-formation with, for example, fumaric acid or maleic acid. The products thus obtained which are usually difficult to solidification or crystallization are collected in a solid form by dissolving the product in a solvent of high solubility, concentrating, adding a solvent of poor solubility, precipitating or solidifying, and drying.

The polymerization degree of the organogermanium compounds of the present invention varies depending upon the conditions of reaction, isolation and purification, and desired one can be obtained by controlling such conditions. The polymerization degree is generally below 50 judging from the molecular weight measured by the light-scattering method, and is in many cases below 6 (especially 3 to 4) by the gel filtration method when measured by dissolving the product in dilute ethanol. The organogermanium compounds having any polymerization degree show essentially same or similar pharmacological effects, but in view of the advantage of purification and pharmaceutical preparations, preferred polymerization degree is below 10.

In many cases, the organogermanium compounds of the invention show no definite melting points, because, during the measurement of the melting point, the products first contract in volume, secondly foam (swell), and lastly discolor.

The organogermanium compounds of the invention are potent in immunomodulatory activities in the form of, for example, potentiating activity for leukocyte migration and accelerating activity for antibody production, which activities permit such compounds to be employed in the treatment of immune diseases, for example, rheumatoid arthritis, autoimmune diseases and bacterial infectious diseases.

The following experiments illustrate that the organogermanium compounds of the invention are useful as agents for treating immune diseases.

1. Test Compounds

A: a polycondensation product of p-(N-methyl-2-ethoxycarbonylacetylamino)phenylgermanium trihydroxide B: a polycondensation product of p-(N-methyl-3-ethoxycarbonylpropionylamino)phenylgermanium trihydroxide C: a polycondensation product of p-(N-ethyl-2-ethoxycarbonylacetylamino)phenylgermanium trihydroxide D: a polycondensation product of p-(N-ethyl-3-ethoxycarbonylpropionylamino)phenylgermanium trihydroxide E: a polycondensation product of p-(N-methyl-3-carboxypropionylamino)phenylgermanium trihydroxide F: a polycondensation product of p-(N-methyl-4-carboxybutyrylamino)phenylgermanium trihydrodie G: a polycondensation product of p-(N-methyl-4-ethoxycarbonylbutyrylamino)phenylgermanium trihydroxide H: a polycondensation product of p-(N-methyl-m-methylbenzoylamino)phenylgermanium trihydroxide Comparison: poly(carboxyethylgermanium sesquioxide)

2. Methods and Results (1) Potentiating Activity for Leukocyte Migration

The test was performed according to the method described by H. Ishikawa et al in "Yakugaku Zasshi (Journal of the Pharmaceutical Society of Japan)", vol. 88, 1472 (1968).

Male Donryu rats weighing about 150 g were divided into groups of 4 to 5 animals each. Five ml of 2% suspension of carboxymethylcellulose (CMC) in physiological saline was injected subcutaneously in the suprascapular area. Compounds tested (0.4 ml/rat) were administered into the CMC pouch immediately after the injection of CMC suspension. Six hours later, 0.1 ml of fluid in the CMC pouch was collected and mixed with 6 ml of 0.05% brilliant cresyl blue solution in phosphate buffer (pH 7.2). The suspension was put in a Bürker chamber and the emigrating leukocytes were counted under a microscope. The percent potentiation was calculated as compared with the count in the control group. The results are shown in Table I.

TABLE I

| Test Compound | Dose mg/rat | Potentiation (%) |
| --- | --- | --- |
| A | 10 | 16 |
|   | 20 | 91 |
| B | 2.5 | 17 |
|   | 5 | 87 |
| C | 0.25 | 7 |
|   | 5 | 87 |
|   | 20 | 96 |
| D | 5 | 7 |
|   | 10 | 33 |
|   | 20 | 210 |
| E | 10 | 26 |
|   | 20 | 47 |
| F | 10 | 44 |
| G | 20 | 56 |
| H | 10 | 46 |
|   | 20 | 55 |
| Comparison | 20 | 13 |

(2) Activity for Antibody Production

C57Bl/6 mice (6 week old, 20 g) were sensitized by intraperitoneally administering sheep red blood cells of $5 \times 10^8/0.1$ ml. Compounds tested were given orally on the same day and next day of the sensitization. Seven days after the sensitization, the number of plaque forming cells (PFC) in spleen and of rosette forming cells (RFC) in spleen and thymus were measured in a usual manner. The results are shown in Table II.

TABLE II

| Test Compound | Dose mg/kg | Control = 100 |||
|---|---|---|---|---|
| | | PFC in Spleen | RFC in Spleen | RFC in Thymus |
| A | 1 | 110 | 157 | 315** |
| | 3 | 125 | 346* | 284* |
| | 30 | 175* | 703** | 431** |
| B | 30 | 81 | 108 | 248* |
| E | 3 | 68 | 86 | 218** |
| F | 3 | 95 | 85 | 141 |
| Comparison | 30 | 100 | 121 | 168 |

*p < 0.05,
**p < 0.01

(3) Prophylactic Effect on Adjuvant Arthritis

The tails of Lewis male rats (250 g) were injected mycobacterium butyricum (0.5 mg/0.1 ml). Compounds tested were orally administered daily from the adjuvant inoculation day (day 1) to day 20. Swellings in the hind feet were measured at 28 days after the adjuvant inoculation. The results are shown in Table III.

TABLE III

| Test Compound | Dose mg/kg | Inhibition (%) |
|---|---|---|
| A | 10 | 22 |
| | 25 | 48** |
| B | 25 | 5 |
| | 100 | 31 |
| E | 25 | 35 |
| | 100 | 53* |
| Comparison | 25 | −18 |
| | 100 | 15 |

(4) Acute Toxicity

TABLE IV

| | Acute Toxicity (rat, per os) ||
|---|---|---|
| Test Compound | Dose mg/kg | Mortality |
| A | 2000 | 0/5 |

The organogermanium compounds of the invention can be used in the form of a pharmaceutical preparation with a suitable and conventional pharmaceutically acceptable carrier. The pharmaceutical preparations can take any conventional form such as tablets, capsules, powder or injectable solutions. The daily dose for human adults usually ranges from about 10 mg to about 1000 mg.

The present invention will be better understood from the following examples, but they are not to be construed as limiting the present invention.

EXAMPLE 1

A mixture of 20 g of p-(methylamino)phenylgermanoic anhydride and 30 g of 2-ethoxycarbonylacetyl chloride in 100 ml of chloroform is stirred at room temperature. An exothermic reaction begins and stirring is continued for 30 minutes. The mixture is heated gradually to boiling and then refluxed vigorously for one hour. The reaction mixture is cooled, and the insoluble matter is filtered off. The filtrate is washed well with a mixture of 30 g of sodium bicarbonate in 200 ml of water, dried over anhydrous magnesium sulfate, and filtered with 10 g of activated charcoal. The filtrate is concentrated, and 60 ml of isopropyl ether is added to the oily residue and boiled. After cooling the solvent is decanted and isopropyl ether is added again to the residue. Solidification is induced by scratching the flask, and the product is ground. The white powder is collected by filtration and dried under reduced pressure for 2 hours to give 24 g of a polycondensation product of p-(N-methyl-2-ethoxycarbonylacetylamino)phenylgermanium trihydroxide. IR (KBr) cm$^{-1}$: 3450 (weak, broad), 2980 (weak, sharp), 1740 (strong), 1595 (middle); NMR (CF$_3$COOH, 100 MHz)$\delta$: 1.36 (3H, t), 3.55 (3H, s), 3.62 (2H, s), 4.34 (2H, q), 7.64 (2H, d), 8.12 (2H, d) [s: singlet, d: doublet, t: triplet, q: quartet, m: multiplet].

EXAMPLE 2

To a suspension of 20 g of p-(methylamino)phenylgermanoic anhydride in 170 ml of chloroform is added dropwise 18 g of 2-ethoxycarbonylacetyl chloride at 0°–15° C. over a 30-minute period. After stirring at room temperature for 2 hours, 130 ml of 2.5% hydrochloric acid is added and stirred vigorously at 5°–15° C. for 30 minutes. The mixture is washed successively with 130 ml of cold water for 10 minutes, 130 ml of 5% aqueous sodium carbonate solution below 15° C. for 30 minutes, and 50 ml of cold water, dried over anhydrous magnesium sulfate, and filtered with activated charcoal. The filtrate is concentrated to about 50 ml on a water bath at 40°–45° C. under reduced pressure. The chloroform solution thus obtained is added dropwise to 500 ml of isopropyl ether over a 30-minute period, and stirred for an additional 30 minutes. The precipitated solid is collected by filtration and dried below 60° C. under reduced pressure to give quantitatively a polycondensation product or p-(N-methyl-2-ethoxycarbonylacetylamino)phenylgermanium trihydroxide.

EXAMPLE 3

Acryloyl chloride (25 g) is added dropwise with stirring at −5° to 0° C. to a suspension of 40 g of p-(methylamino)phenylgermanoic anhydride in 300 ml of chloroform. The stirring is continued at −5° to 0° C. for 30 minutes, at room temperature for one hour, and then under reflux for one hour. The reaction mixture is washed successively with 100 ml of cold 3% hydrochloric acid, 100 ml of cold water and 100 ml of 5% potassium carbonate solution, quickly dried over anhydrous potassium carbonate, and the chloroform is distilled off under reduced pressure. Isopropyl ether is added to the residue and the whole is stirred. The resulting solid is ground to give 46 g of a polycondensation product of p-(N-methyl-acryloylamino)phenylgermanium trihydroxide. NMR (CF$_3$COOH, 100 MHz)$\delta$: 3.67 (3H, s), 6.15 (2H, q), 6.62 (1H, d), 7.63 (2H, d), 8.15 (2H, d).

EXAMPLE 4

Bromoacetyl bromide (42 g) is added dropwise with stirring at 0° C. to a suspension of 40 g of p-(methylamino)phenylgermanoic anhydride in 300 ml of chloroform. The stirring is continued at 0° C. for 30 minutes, at room temperature for one hour and then reflux for one hour. The insoluble matter is filtered off, and the filtrate is washed successively with 100 ml of water, 100 ml of 4% sodium bicarbonate solution, and 100 ml of cold water, and dried over anhydrous magnesium sulfate and concentrated under reduced pressure. Isopropyl ether is added to the remaining oil. The resulting solid is ground to give 57 g of a polycondensation product of p-(N-methyl-bromoacetylamino)-phenylgermanium trihydroxide. NMR (CDCl$_3$, 100 MHz)$\delta$: 3.52 (3H, s), 3.85 (2H, s), 7.74 (2H, d), 8.15 (2H, d).

EXAMPLE 5

A mixture of 15 g of 3-chloropropionyl chloride and 20 g of p-(methylamino)phenylgermanoic anhydride in 150 ml of benzene is refluxed for 2 hours. After cooling, 200 ml of water is added to the reaction mixture and the whole is stirred well. The oil insoluble in benzene and water is collected, washed with water and with a sodium bicarbonate solution, and extracted with chloroform. The extract is concentrated, isopropyl ether is added to the residue, and the whole is stirred. Thus is obtained 27 g of a polycondensation product of p-(N-methyl-3-chloropropionylamino)phenylgermanium trihydroxide as a white powder. IR (KBr) cm$^{-1}$: 3350 (weak, sharp), 2900 (weak, sharp), 1650 (strong, sharp), 1595 (strong, sharp), 1500 (middle, sharp); NMR (CF$_3$COOH, 100 MHz)δ: 2.12 (2H, m), 3.45 (2H, m), 3.58 (3H, s), 7.62 (2H, d), 8.12 (2H, d).

EXAMPLE 6

A mixture of 4.0 g of 3-ethoxycarbonylpropionyl chloride and 3.0 g of p-(methylamino)phenylgermanoic anhydride in 20 ml of chloroform is stirred at room temperature for 30 minutes and then refluxed for 2 hours. After cooling, the reaction mixture is stirred well for 5 minutes with 20 ml of 5% hydrochloric acid. The resulting mixture is washed with 20 ml of water and with 50 ml of 5% sodium bicarbonate solution. The chloroform is distilled off, and isopropyl ether is added to the residue. The resulting solid is ground to give 4.3 g of a polycondensation product of p-(N-methyl-3-ethoxycarbonylpropionylamino)phenylgermanium trihydroxide as a white powder. IR (KBr) cm$^{-1}$: 3450 (weak, sharp), 2950 (weak, sharp), 1730 (strong, sharp), 1660 (strong, sharp), 1595 (middle, sharp); NMR (CF$_3$COOH, 100 MHz)δ: 1.34 (3H, t), 2.56 (4H, m), 3.58 (3H, s), 4.32 (2H, q), 7.62 (2H, d), 8.12 (2H, d).

EXAMPLE 7

A solution of 3.3 g of potassium hydroxide in 10 ml of methanol is added to a solution of 3.3 g of a polycondensation product of p-(N-methyl-3-ethoxycarbonylpropionylamino)phenylgermanium trihydroxide in 30 ml of methanol, and the resulting mixture is stirred at room temperature for 3 hours. The methanol is distilled off under reduced pressure, 50 ml of water is added to the residue and filtered with activated charcoal. The insoluble matter is filtered off, and the filtrate is made acidic with dilute hydrochloric acid. The separated oil is collected by decantation, washed with water, and dissolved in 30 ml of isopropanol. The insoluble matter is filtered off, the filtrate is concentrated under reduced pressure, and isopropyl ether is added to the residual oil. The resulting solid is ground to give 2.1 g of a polycondensation product of p-(N-methyl-3-carboxypropionylamino)phenylgermanium trihydroxide as a hygroscopic glassy powder. IR (KBr) cm$^{-1}$: 3000–3600 (middle, broad), 2930 (middle, sharp), 1730 (strong, sharp), 1655 (strong, sharp), 1620 (middle, sharp), 1590 (strong, sharp), 1500 (middle, sharp); NMR (CF$_3$COOH, 100 MHz)δ: 2.12 (2H, m), 2.60 (4H, m), 3.58 (3H, s), 7.64 (2H, d), 8.12 (2H, d).

EXAMPLE 8

A mixture of 10 g of m-methylbenzoyl chloride and 6 g of p-(methylamino)phenylgermanoic anhydride in 40 ml of benzene is stirred at room temperature for 30 minutes and then refluxed for 3 hours. After cooling, 100 ml of water is added to the reaction mixture. The separated oil is collected, washed with 5% sodium hydroxide solution, and dissolved in 50 ml of chloroform. The chloroform layer is washed with water, and concentrated. Isopropyl ether is added to the residue. The resulting solid is ground to give 9.1 g of a polycondensation product of p-(N-methyl-m-methylbenzoylamino)phenylgermanium trihydroxide as a white powder. IR (KBr) cm$^{-1}$: 3450 (weak, broad), 2900 (weak, sharp), 1650 (strong, sharp), 1590 (middle, sharp); NMR (CF$_3$COOH, 100 MHz)δ: 2.34 (3H, s), 3.80 (3H, s), 7.32 (4H, m), 7.52 (2H, d), 7.92 (2H, d).

EXAMPLE 9

A mixture of 10 g of cinnamoyl chloride and 7 g of p-(methylamino)phenylgermanoic anhydride in 40 ml of benzene is refluxed for 3 hours. The reaction mixture is then stirred with 100 ml of 5% sodium bicarbonate solution. The separated oil is collected and extracted with chloroform. The extract is dried, and concentrated. The residue is extracted with hot ethyl acetate, and a small amount of ethanol is added to the residue. The resulting solid is ground to give 10 g of a polycondensation product of p-(N-methyl-cinnamoylamino)phenylgermanium trihydroxide as a white powder. IR (KBr) cm$^{-1}$: 3050 (weak, sharp), 1760 (strong, sharp), 1700 (middle, sharp), 1630 (middle, sharp); NMR (CF$_3$COOH, 100 MHz)δ: 3.72 (3H, s), 6.44 (1H, d), 3.46 (5H, s), 7.68 (2H, d), 7.93 (1H, d), 8.15 (2H, d).

EXAMPLE 10

A mixture of 14.6 g of 2-(p-chlorophenoxy)-2-methylpropionyl chloride and 6.0 g of p-(methylamino)phenylgermanoic anhydride in 100 ml of chloroform is refluxed for 3 hours. After cooling, the reaction mixture is washed with 100 ml of water, dried and concentrated. To the residue is added 10 ml of ethanol, and the whole is allowed to stand overnight. The ethanol is distilled off, and the residue is stirred with 100 ml of water and extracted with 70 ml of chloroform. The chloroform is distilled off, the residue is extracted with hot isopropyl ether to remove the soluble matter and cooled. The resulting solid is ground and the powder is stirred well in hexane to give 11 g of a polycondensation product of p-[N-methyl-2-(p-chlorophenoxy)-2-methylpropionylamino]phenylgermanium trihydroxide as a white powder. NMR (CF$_3$COOH, 100 MHz)δ: 1.78 (6H, s), 3.58 (3H, s), 7.0 (4H, m), 7.41 (2H, d), 7.90 (2H, s).

EXAMPLE 11

3.6 g of 2-ethoxycarbonylacetyl chloride and 4.0 g of p-(ethylamino)phenylgermanoic anhydride are mixed at 0° C. in 30 ml of chloroform. After one hour, the mixture is stirred at 30°–40° C. for one hour. The reaction mixture is cooled to 20° C. whereupon 30 ml of 5% hydrochloric acid is added, and stirred for 15 minutes, washed with 30 ml of water and with 30 ml of 5% sodium bicarbonate solution, dried and concentrated. Isopropyl ether is added to the residue. The resulting solid is ground to give 5.9 g of a polycondensation product of p-(N-ethyl-2-ethoxycarbonylacetylamino)phenylgermanium trihydroxide as a white powder. NMR (CF$_3$COOH, 100 MHz)δ: 1.35 (6H, m), 3.60 (3H, s), 4.05 (2H, q), 4.36 (2H, q), 7.64 (2H, d), 8.15 (2H, d).

The following germanium compounds are produced in an analogous manner of Example 1 to 11.

(12) a polycondensation product of p-(N-methyl-4-chlorobutyrylamino)phenylgermanium trihydroxide, IR (KBr) cm$^{-1}$: 3350 (weak, sharp), 2900 (weak, sharp), 1650 (strong, sharp), 1590 (weak, sharp), 1500 (middle, sharp); NMR (CF$_3$COOH, 100 MHz)δ: 2.10 (2H, m), 2.56 (2H, m), 3.45 (2H, m), 3.58 (3H, s), 7.62 (2H, d), 8.12 (2H, d)

(13) a polycondensation product of p-(N-methyl-4-ethoxycarbonylbutyrylamino)phenylgermanium trihydroxide, IR (KBr) cm$^{-1}$: 3450 (weak, broad), 2950 (weak, sharp), 1730 (strong, sharp), 1660 (strong, sharp), 1595 (middle, sharp); NMR (CF$_3$COOH, 100 MHz)δ: 1.34 (3H, t), 2.10 (2H, m), 2.56 (4H, m), 3.58 (3H, s), 4.32 (2H, q), 7.62 (2H, d), 8.12 (2H, d)

(14) a polycondensation product of p-(N-methyl-5-methoxycarbonylpentanoylamino)phenylgermanium trihydroxide, IR (KBr) cm$^{-1}$: 2950 (weak, sharp), 1740 (strong, sharp), 1660 (strong, broad), 1600 (middle, sharp), 1500 (middle, sharp), 900 (middle, broad); NMR (CF$_3$COOH, 100 MHz)δ: 1.75 (4H, m), 2.50 (4H, m), 3.55 (3H, s), 3.83 (3H, s), 7.61 (2H, d), 8.12 (2H, d)

(15) a polycondensation product of p-(N-methyl-4-carboxybutyrylamino)phenylgermanium trihydroxide, IR (KBr) cm$^{-1}$: 3000 (middle, broad), 1730 (strong, sharp), 1650 (strong, sharp), 1620 (middle, sharp), 1580 (strong, sharp); NMR (CF$_3$COOH, 100 MHz)δ: 2.14 (2H, m), 2.58 (4H, m), 3.58 (3H, s), 7.62 (2H, d), 8.12 (2H, d)

(16) a polycondensation product of p-(N-methyl-m-carboxybenzoylamino)phenylgermanium trihydroxide, IR (KBr) cm$^{-1}$: 2800-3600 (middle, broad), 1720 (strong, sharp), 1650 (strong, sharp), 1595 (middle, sharp); NMR (CF$_3$COOH, 100 MHz)δ: 3.72 (3H, s), 7.30 (1H, s), 7.45 (3H, s), 7.85 (2H, d), 8.19 (2H, d)

(17) a polycondensation product of p-(N-methyl-m-ethoxycarboxylbenzoylamino)phenylgermanium trihydroxide

(18) a polycondensation product of p-(N-methyl-benzoylamino)phenylgermanium trihydroxide, IR (KBr) cm$^{-1}$: 3450 (weak, broad), 2940 (weak, sharp), 1650 (strong, sharp), 1590 (middle, sharp); NMR (CF$_3$COOH, 100 MHz)δ: 3.80 (3H, s), 7.33 (5H, s), 7.62 (2H, d), 8.12 (2H, d)

(19) a polycondensation product of p-[N-methyl-2,2-dimethyl-3-(2-methyl-1-propenyl)cyclopropylcarbonylamino]phenylgermanium trihydroxide, IR (KBr) cm$^{-1}$: 2900 (weak, sharp), 1655 (strong, sharp), 1590 (middle, sharp); NMR (CDCl$_3$, 100 MHz)δ: 0.95 (3H, s), 1.25 (3H, s), 1.64 (3H, s),

(20) a polycondensation product of p-(N-butyl-2-ethoxycarbonylacetylamino)phenylgermanium trihydroxide, NMR (CF$_3$COOH, 100 MHz)δ: 1.00 (3H, t), 1.35 (3H, t), 1.45 (2H, m), 1.75 (2H, m), 3.60 (3H, s), 4.05 (2H, q), 4.20 (2H, m), 7.64 (2H, d), 8.15 (2H, d)

(21) a polycondensation product of p-(N-ethyl-m-methylbenzoylamino)phenylgermanium trihydroxide, NMR (CF$_3$COOH, 100 MHz)δ: 1.40 (3H, t), 2.30 (3H, s), 4.27 (3H, s), 7.28 (4H, m), 7.50 (2H, d), 7.90 (2H, d)

(22) a polycondensation product of p-(N-butyl-m-methylbenzoylamino)phenylgermanium trihydroxide, NMR (CF$_3$COOH, 100 MHz)δ: 1.00 (3H, t), 1.45 (2H, m), 1.75 (2H, m), 2.30 (3H, s), 4.20 (2H, m), 7.24 (5H, s), 7.45 (2H, d), 7.85 (2H, d)

(23) a polycondensation product of p-(N-methyl-dichloroacetylamino)phenylgermanium trihydroxide, IR (KBr) cm$^{-1}$: 3000 (weak, broad), 2900 (weak, sharp), 1690 (strong, sharp), 1590 (middle, sharp); NMR (CF$_3$COOH, 100 MHz)δ: 3.52 (3H, s), 5.96 (1H, s), 7.68 (2H, d), 8.13 (2H, d)

(24) a polycondensation product of p-(N-methylacetylamino)phenylgermanium trihydroxide, IR (KBr) cm$^{-1}$: 3300 (weak, broad), 2950 (weak, sharp), 1660 (strong, sharp), 1590 (middle, sharp), 1500 (middle, sharp); NMR (CF$_3$COOH, 100 MHz)δ: 2.35 (3H, s), 3.63 (3H, s), 7.66 (2H, d), 8.17 (2H, d)

(25) a polycondensation product of p-(N-methyl-pivaloylamino)phenylgermanium trihydroxide, NMR (CF$_3$COOH, 100 MHz)δ: 1.34 (9H, m), 3.64 (3H, s), 7.70 (2H, d), 8.15 (2H, d)

(26) a polycondensation product of p-(N-ethyl-4-ethoxybutyrylamino)phenylgermanium trihydroxide, NMR (CF$_3$COOH, 100 MHz)δ: 1.41 (6H, t), 2.10 (2H, m), 2.61 (4H, m), 4.10 (2H, q), 4.35 (2H, q), 7.64 (2H, d), 8.19 (2H, d)

(27) a polycondensation product of p-(N-ethyl-3-ethoxypropionylamino)phenylgermanium trihydroxide, NMR (CF$_3$COOH, 100 MHz)δ: 1.34 (3H, t), 1.40 (3H, t), 2.88 (2H, m), 4.09 (2H, q), 4.40 (2H, q), 7.64 (2H, d), 8.16 (2H, d)

(28) a polycondensation product of p-(N-methyl-p-methoxybenzoylamino)phenylgermanium trihydroxide

(29) a polycondensation product of p-(N-methyl-3,4,5-trimethoxybenzoylamino)phenylgermanium trihydroxide

(30) a polycondensation product of p-(N-methyl-p-iodobenzoylamino)phenylgermanium trihydroxide

(31) a polycondensation product of p-(N-methyl-2-chloro-4-nitrobenzoylamino)phenylgermanium trihydroxide

(32) a polycondensation product of p-(N-methyl-p-cyanobenzoylamino)phenylgermanium trihydroxide

(33) a polycondensation product of p-(N-methyl-cyclohexylcarbonylamino)phenylgermanium trihydroxide

(34) a polycondensation product of p-(N-methyl-p-acetylaminobenzoylamino)phenylgermanium trihydroxide

(35) a polycondensation product of p-(N-methyl-2-furoylamino)phenylgermanium trihydroxide

(36) a polycondensation product of p-(N-methyl-2-thenoylamino)phenylgermanium trihydroxide

(37) a polycondensation product of p-(N-methyl-nicotinoylamino)phenylgermanium trihydroxide, NMR (CF$_3$COOH, 100 MHz)δ: 3.77 (3H, s), 7.58 (2H, d), 7.95 (2H, d), 8.60 (1H), 8.85 (2H), 9.03 (1H)

(38) a polycondensation product of p-(N-methyl-4-phenyl-4-oxobutyrylamino)phenylgermanium trihydroxide

(39) a polycondensation product of p-[N-methyl-2-(o-nitrophenylthio)acetylamino]phenylgermanium trihydroxide

(40) a polycondensation product of p-[N-methyl-(N-benzoylglycyl)amino]phenylgermanium trihydroxide

(41) a polycondensation product of p-[N-methyl-4-(acetylaminomethyl)cyclohexylcarbonylamino]-phenylgermanium trihydroxide

EXAMPLE 42

A solution of 4 ml of 20% dimethylamine-ethanol and 2.0 g of a polycondensation product of p-(N-methylacryloylamino)phenylgermanium trihydroxide in 20 ml of ethanol is allowed to stand for one day, and then the ethanol is distilled off. To the residue are added 20 ml of water and 1.5 of maleic acid. Activated charcoal is added to the resulting solution, and filtered. The filtrate is neutralized with sodium carbonate and extracted with three 20-ml portions of chloroform. The combined extracts are dried and concentrated. To the residue is added a solution of 1.4 g of fumaric acid in 20 ml of methanol, and the whole is stirred. The methanol is removed, and 10 ml of water is added to the residue. The insoluble matter is filtered off, and the filtrate is concentrated to give 2.2 g of the fumaric acid salt of a polycondensation product of p-(N-methyl-3-dimethylaminopropionylamino)phenylgermanium trihydroxide as a white powder. IR (KBr) cm$^{-1}$: 3420 (weak, broad), 3040 & 2950 (weak, sharp), 1700 (middle, sharp), 1650 (strong, sharp), 1590 (strong, sharp); NMR (D$_2$O, 100 MHz)δ: 2.64 (2H, t), 2.84 (6H, s), 3.28 (3H, s), 3.39 (2H, d), 6.66 (2H, s), 7.50 (2H, d), 7.80 (2H, d)

EXAMPLE 43

A mixture of 2.6 g of N-(m-trifluoromethylphenyl)-piperazine and 2.6 g of a polycondensation product of p-(N-methyl-acryloylamino)phenylgermanium trihydroxide in 20 ml of ethanol is refluxed for 2 hours. To the reaction mixture is added 3.0 g of maleic acid and the ethanol is distilled off under reduced pressure. The residue is washed with three 15-ml portions of water, dissolved in 30 ml of isopropanol and concentrated (these procedures are repeated once again). Isopropyl ether is added to the residue. The resulting solid is ground to give 4.3 g of the maleic acid salt of a polycondensation product of p-[N-methyl-3-(4-m-trifluoromethylphenyl-1-piperazinyl)propionylamino]phenylgermanium trihydroxide. IR (KBr) cm$^{-1}$: 3400 (weak, broad), 3000 (weak, broad), 2500 (weak, broad), 1720 (middle, sharp), 1650 (strong, sharp), 1590 (strong, sharp); NMR (CF$_3$COOH, 100 MHz)δ: 3.00 (2H, m), 3.50 (3H, s), 3.80 (m), 4.40 (m), 6.63 (3H, s), 7.60 (2H, d), 8.00 (6H, d+m).

EXAMPLE 44

A mixture of 1.5 g of N-benzylpiperazine and 2 g of a polycondensation product of p-(N-methyl-acryloylamino)phenylgermanium trihydroxide in 15 ml of ethanol is refluxed for 2 hours. After cooling, a solution of 2 g of maleic acid in 10 ml of ethanol is added to the reaction mixture. The resulting crystals are collected by filtration, washed with three 10-ml portions of water, and recrystallized from ethanol to give 4.9 g of the maleic acid salt of a polycondensation product of p-[N-methyl-3-(4-benzyl-1-piperazinyl)propionylamino]phenylgermanium trihydroxide. IR (KBr) cm$^{-1}$: 3400 (weak, broad), 3000 (weak, sharp), 2400 (weak, broad), 1700 (middle, sharp), 1650 (middle, sharp), 1620 (middle, sharp), 1580 (strong, sharp), 1460 (strong, sharp).

EXAMPLE 45

A mixture of 1.8 g of 4-phenyl-4-piperidinol and 2.6 g of p-(N-methyl-acryloylamino)phenylgermanium trihydroxide in 10 ml of ethanol is refluxed for 2 hours. To the reaction mixture is added 1.5 g of maleic acid, and the ethanol is distilled off under reduced pressure. The residue is washed with three 10-ml portions of water. The residual oil is dissolved in 50 ml of isopropanol, and concentrated, and ethyl acetate is added to the residue. The resulting solid is ground to give 3.8 g of the maleic acid salt of a polycondensation product of p-[N-methyl-3-(4-hydroxy-4-phenylpiperidino)propionylamino]phenylgermanium trihydroxide. IR (KBr) cm$^{-1}$: 3400 (middle, broad), 3040 (weak, sharp), 3000 (weak, sharp), 1700 (middle, sharp), 1650 (strong, sharp), 1590 (strong, sharp), 1450–1500 (strong); NMR (CF$_3$COOH, 100 MHz)δ: 2.90 (m), 3.48 (3H, s), 3.60 (s), 3.80 (m), 6.64 (2H, s), 7.50 (5H, m), 7.62 (2H, d), 8.15 (2H, d).

EXAMPLE 46

A mixture of 3.8 g of N-benzoylpiperazine, 6.2 g of a polycondensation product of p-(N-methyl-2-bromoacetylamino)phenylgermanium trihydroxide and 3 g of potassium carbonate in 40 ml of ethanol is stirred at room temperature for 4 hours and then refluxed for one hour. After cooling, the insoluble matter is filtered off, and 3 g of maleic acid is added to the filtrate. The whole is allowed to stand. The oil separated is collected, washed with three 3-ml portions of cold water, and 50 ml of warm water is added and neutralized with potassium carbonate and extracted with three 30-ml portions of chloroform. The combined extracts are dried, treated with activated charcoal, and concentrated. The resulting solid is ground to give 5.5 g of a polycondensation product of p-[N-methyl-2-(4-benzoyl-1-piperazinyl)acetylamino]phenylgermanium trihydroxide. IR (KBr) cm$^{-1}$: 3450 (weak, broad), 2950 (weak, sharp), 2800 (weak, sharp), 1660 (strong, sharp), 1620 (strong, sharp), 1590 (middle, sharp), 1490 (middle, sharp), 1420 (middle, sharp); NMR (CF$_3$COOD, 100 MHz)δ: 3.50 (3H, s), 3.60–4.20 (10H, m), 7.40–7.60 (7H, m), 8.10 (2H, d).

The following germanium compounds are produced in an analogous manner of Examples 42 to 46.

(47) a polycondensation product of p-(N-methyl-3-diethylaminopropionylamino)phenylgermanium trihydroxide

(48) a polycondensation product of p-(N-methyl-3-piperidinopropionylamino)phenylgermanium trihydroxide

(49) a polycondensation product of p-[N-methyl-3-(4-methyl-1-piperazinyl)propionylamino]phenylgermanium trihydroxide

(50) a polycondensation product of p-(N-methyl-3-dimethylamino-2-methylpropionylamino)phenylgermanium trihydroxide

(51) a polycondensation product of p-[N-methyl-3-(4-o-methoxyphenyl-1-piperazinyl)propionylamino]-phenylgermanium trihydroxide, IR (KBr) cm$^{-1}$: 3400 (weak, broad), 2950 (weak, sharp), 2820 (weak, sharp), 1700 (weak, sharp), 1650 (strong, sharp), 1590 (strong, sharp), 1500 (strong, sharp), 1450 (strong, sharp); NMR (CF$_3$COOH, 100 MHz)δ: 2.95 (2H, m), 2.48 (3H, s), 4.04 (3H, s), 4.28 (m), 6.62 (2H, s), 7.24 (2H), 7.60 (4H, m), 8.10 (2H, d)

(52) maleic acid salt of a polycondensation product of p-[N-methyl-3-(4-phenethyl-1-piperazinyl)propionylamino]phenylgermanium trihydroxide

(53) maleic acid salt of a polycondensation product of p-[N-methyl-3-(4-(3-phenylpropyl)-1-piperazinyl)-propionylamino]phenylgermanium trihydroxide, IR (KBr) cm$^{-1}$: 3400 (weak, broad), 3000 (weak, sharp), 2920 (weak, sharp), 2400 (weak, broad), 1700 (middle, sharp), 1650 (strong, sharp), 1620 (sharp), 1580 (strong, sharp), 1470 (strong, broad); NMR (CF$_3$COOH, 100 MHz)δ: 2.24 (2H, m), 2.85 (4H, m), 3.45 (3H, s), 3.75 (m), 4.15 (m), 6.65 (4H, s), 7.25 (5H, m), 7.58 (2H, d), 8.10 (2H, d)

(54) maleic acid salt of a polycondensation product of p-[N-methyl-3-(4-benzoyl-1-piperazinyl)propionylamino]phenylgermanium trihydroxide, IR (KBr) cm$^{-1}$: 3400 (weak, broad), 2950 (weak, sharp), 1700 (middle, sharp), 1650 (strong, sharp), 1590 (strong, sharp), 1500 (strong, sharp), 1450 (strong, broad); NMR (CF$_3$COOH, 100 MHz)δ: 2.90 (2H, m), 3.45 (3H, s), 3.60 (m), 3.90 (m), 6.64 (2H, s), 7.54 (6H, s), 7.60 (1H, s), 8.10 (2H, d)

(55) a polycondensation product of p-[N-ethyl-3-(4-benzoyl-1-piperazinyl)-2-methylpropionylamino]-phenylgermanium trihydroxide

(56) maleic acid salt of a polycondensation product of p-[N-methyl-3-(4-(2,3-dihydro-2-oxobenzimidazol-1-yl)piperidino)propionylamino]phenylgermanium trihydroxide, IR (KBr) cm$^{-1}$: 3000-3400 (weak), 1700 (strong, sharp), 1660 (middle, sharp), 1590 (middle, sharp), 1480 (strong, sharp); NMR (CF$_3$COOH, 100 MHz)δ: 2.40 (2H, m), 2.95 (2H, m), 3.30 (m), 3.50 (3H, s), 4.00 (m), 6.63 (2H, s), 7.35 (4H, m), 7.60 (2H, d), 8.10 (2H, d)

(57) a polycondensation product of p-[N-methyl-3-(4-benzoylamino-piperidino)propionylamino]phenylgermanium trihydroxide

(58) a polycondensation product of p-[N-methyl-3-(4-aminobenzoylaminopiperidino)propionylamino]-phenylgermanium trihydroxide

(59) a polycondensation product of p-[N-methyl-2-(4-phenethyl-1-piperazinyl)acetylamino]phenylgermanium trihydroxide, IR (KBr) cm$^{-1}$: 3400-3500 (weak), 2900-3050 (weak), 1620-1670 (strong), 1590 (strong, sharp), 1500 (middle, sharp), 1420-1460 (middle); NMR (CF$_3$COOH, 100 MHz)δ: 3.20 (2H, m), 3.50 (3H, s), 3.70-4.30 (m), 7.35 (5H, m), 7.65 (2H, d), 8.15 (2H, d)

Although the present invention has been adequately discussed in the foregoing specification and examples included therein, one readily recognizes that various changes and modifications may be made without departing from the spirit and scope thereof.

What is claimed is:

1. A polycondensation product of a germanium trihydroxide compound of the formula:

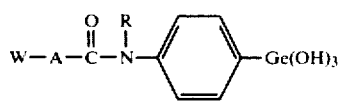

wherein W is hydrogen, alkyl, halogen, alkoxycarbonyl, carboxy, aryl, cycloalkyl which may be substituted, cycloalkenyl, heteroaryl or a group of the formula: (R$^1$)(R$^2$)N— wherein R$^1$ and R$^2$ are each lower alkyl or R$^1$ and R$^2$ together with the adjacent nitrogen atom form a group of the formula:

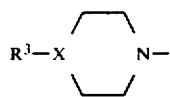

wherein R$^3$ is hydrogen, lower alkyl, phenyl which may be substituted, aralkyl, acyl, acylamino or heteroaryl, X is —N=, —CH= or

A is a bond, alkylene, alkenylene, —CO—Y—, —CONH—Y—, —O—Y—, —S—Y— or

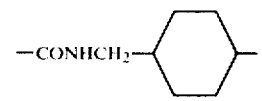

where Y is alkylene; and R is alkyl.

2. The polycondensation product of claim 1 wherein W is alkoxycarbonyl and A is alkylene.

3. The polycondensation product of claim 1, wherein said product is a polycondensation product of p-(N-methyl-2-ethoxycarbonylacetylamino)-phenylgermanium trihydroxide.

4. The polycondensation product of claim 1, wherein said product is a polycondensation product of p-(N-methyl-3-ethoxycarbonylpropionylamino)-phenylgermanium trihydroxide.

5. The polycondensation product of claim 1, wherein said product is a polycondensation product of p-(N-ethyl-2-ethoxycarbonylacetylamino)-phenylgermanium trihydroxide.

6. The polycondensation product of claim 1, wherein said product is a polycondensation product of p-(N-ethyl-3-ethoxycarbonylpropionylamino)-phenylgermanium trihydroxide.

7. The polycondensation product of claim 1, wherein said product is a polycondensation product of p-(N-methyl-3-carboxypropionylamino)-phenylgermanium trihydroxide.

8. The polycondensation product of claim 1, wherein said product is a polycondensation product of p-(N-methyl-4-carboxybutyrylamino)-phenylgermanium trihydroxide.

9. The polycondensation product of claim 1, wherein said product is a polycondensation product of p-(N-methyl-4-ethoxycarbonylbutyrylamino)-phenylgermanium trihydroxide.

10. The polycondensation product of claim 1, wherein said product is a polycondensation product of p-(N-methyl-m-methylbenzoylamino)-phenylgermanium trihydroxide.

11. A pharmaceutical composition for treating rheumoid arthritis in humans comprising an effective amount of the polycondensation product of claim 1 in combination with a pharmaceutically acceptable carrier.

12. A method for producing a polycondensation product of a germanium trihydroxide compound of the formula:

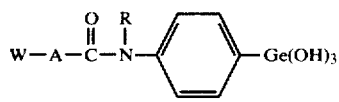

wherein W is hydrogen, alkyl, halogen, alkoxycarbonyl, aryl, cycloalkyl which may be substituted, cycloalkenyl or heteroaryl, A is a bond, alkylene, alkenylene, —CO—Y, —CONH—Y—, —O—Y—, —S—Y— or —CONHCH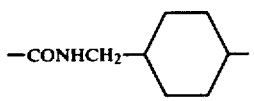
and R is alkyl, which comprises reacting a compound of the formula:
(RNH—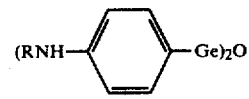—Ge)$_2$O
wherein R is as defined above, with a functional derivative of a carboxylic acid of the formula:
W—A—COOH
wherein A and W are as defined above.
* * * * *